(12) United States Patent
Shohet et al.

(10) Patent No.: US 6,191,103 B1
(45) Date of Patent: Feb. 20, 2001

(54) METHODS FOR ENHANCING THROMBOLYSIS IN A MAMMAL

(75) Inventors: Stephen B. Shohet, San Francisco; Irwin Sherman, Riverside, both of CA (US); Ulrich von Andrian, Brookline, MA (US)

(73) Assignees: The Regents of the University of California, Oakland, CA (US); Center for Blood Research, Boston, MA (US)

( * ) Notice: Under 35 U.S.C. 154(b), the term of this patent shall be extended for 0 days.

(21) Appl. No.: 08/985,499

(22) Filed: Dec. 5, 1997

(51) Int. Cl.[7] .................................................. A61K 38/00
(52) U.S. Cl. .................. 514/2; 514/12; 514/13; 514/14; 514/15; 514/16; 514/822
(58) Field of Search .................................. 514/2, 12, 13, 514/14, 15, 16, 822

(56) References Cited

FOREIGN PATENT DOCUMENTS

9629086 * 9/1996 (WO).

OTHER PUBLICATIONS

Crandall, Ian et al., *Proc. Natl. Acad. Sci. USA*, 90:4703–4707 (1993).
Ito, S. et al., *The International Journal of Artificial Organs*, 15 (12) :737–745 (1992).
Land, K.M. et al., *Parasitology Today*, 11 (1) :19–23 (1995).
Thevenin, B.J.-M. et al., SS Boston National Sickle Cell Program, Abstract, "A Peptide Comprising Residues 546–553 of Human Erythrocyte Band 3 Inhibits Sickle Cell Adherence to the Endothelium," Mar. 18–21, (1995).
Thevenin, B.J.-M. et al., Assn. American Physicians San Diego Clinical Res. Mtg., Abstract, "Inhibition of Sickle Cell Cytoadherence by Peptides from Exofacially Exposed Sites of Band 3," May 5–8, (1995).
"Taking the bite out of killer malaria, " *The Press–Enterprise*, May 15, 1993.
"UC Scientists Block Attachment of Malaria–Infected Cells to Endothelium," *Genetic Engineering News*, Jun. 1, 1993.

* cited by examiner

*Primary Examiner*—Dwayne C. Jones
*Assistant Examiner*—C. Delacroix-Muirheid
(74) *Attorney, Agent, or Firm*—Townsend and Townsend and Crew LLP

(57) ABSTRACT

It has been found that agents which inhibit the interaction between the band 3 protein and its ligand (hereafter sometimes referred to as "interaction inhibitors" or "inhibitors"), CD36/thrombospondin, can also be used to enhance thrombolysis. The inhibitors can be peptides which contain sequences present in exofacial loops of the band 3 protein, or can be non-natural, D-isomer forms of the same sequences, or can be peptides, peptidomimetics, or non-peptidic molecules which interfere with band 3 protein—ligand interactions. One preferred group of such inhibitors comprises peptides characterized by the sequence motif $Z^2Z^3Z^2UX^-UUUX^-$ (SEQ ID NO:44), wherein $Z^2$ represents a hydrophobic residue, U represents unobstructive residues, $Z^3$ is either $Z^2$ or an unobstructive residue and $X^-$ represents negatively charged residues. Another preferred group of such inhibitors comprises peptides characterized by the sequence motif $Z^1UKUUUX^+$ (SEQ ID NO:45), wherein $Z^1$ is selected from the group consisting of tyrosine, phenylalanine and alanine; K is a lysine residue; U represents unobstructive residues; and $X^+$ is a positively charged residue. The reverse sequences of these peptides are also active. The inhibitors of the subject method can be administered alone or in combination with one or more additional therapeutic agents. Administration can be oral, intravenous or by other means, in amounts between about 0.1 mg/kg to about 20 mg/kg.

31 Claims, 1 Drawing Sheet

SEQUENCE LISTING (1) GENERAL INFORMATION:

(iii) NUMBER OF SEQUENCES: 45

(2) INFORMATION FOR SEQ ID NO:1:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:1:

His Pro Leu Gln Lys Thr Tyr
1               5

(2) INFORMATION FOR SEQ ID NO:2:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

Tyr Val Lys Arg Val Lys
1               5

(2) INFORMATION FOR SEQ ID NO:3:

(i) SEQUENCE CHARACTERISTICS:
        (A) LENGTH: 3 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Tyr Val Lys
1

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

His Pro Gln Lys Thr Tyr
1               5

(2) INFORMATION FOR SEQ ID NO:5:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: one-of(1, 3)
        (D) OTHER INFORMATION: /product= "OTHER"
            /note= "Xaa = hydrophobic amino acid,
            e.g., Phe, Ala, Val, Leu or Ile"

(ix) FEATURE:
        (A) NAME/KEY: Modified-site
        (B) LOCATION: one-of(2, 4, 6, 7, 8, 9)
        (D) OTHER INFORMATION: /product= "OTHER"
            /note= "Xaa = unobstructive amino acid
            selected from the group consisting of
            Ala, Val, Leu, Ile, Met, Gly, Ser, Thr,
            Arg, Cys, Gln or Asn"

(ix) FEATURE:
        (A) NAME/KEY: Modified-site
        (B) LOCATION: one-of(5, 10)
        (D) OTHER INFORMATION: /product= "OTHER"
            /note= "Xaa = negatively charged amino
            acid, e.g., Glu or Asp"

(xi) SEQUENCE DESCRIPTION: SEQ ID NO:5:

Xaa Xaa Xaa Xaa Xaa Xaa Xaa Xaa Xaa Xaa
1               5                   10

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS:
        (D) TOPOLOGY: linear

```
        (ii) MOLECULE TYPE: peptide (xi) SEQUENCE DESCRIPTION: SEQ ID NO:6:

Asp His Pro Leu Gln Lys Thr Tyr Asn Tyr
1               5                   10

(2) INFORMATION FOR SEQ ID NO:7:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:7:

Tyr Thr Gln Lys Leu Ser Val Pro Asp Gly Phe Lys Val Ser Asn
1               5                   10                  15

(2) INFORMATION FOR SEQ ID NO:8:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:8:

Lys Leu Ile Lys Ile Phe Gln Asp His Pro Leu Gln Lys Thr Tyr
1               5                   10                  15

(2) INFORMATION FOR SEQ ID NO:9:

(i) SEQUENCE CHARACTERISTICS:
            (A) LENGTH: 14 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:9:

Lys Pro Pro Lys Tyr His Pro Asp Val Pro Tyr Val Lys Arg
1               5                   10

(2) INFORMATION FOR SEQ ID NO:10:

(i) SEQUENCE CHARACTERISTICS:
            (A) LENGTH: 14 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:10:

Asp Val Pro Tyr Val Lys Arg Val Lys Thr Trp Arg Met His
1               5                   10

(2) INFORMATION FOR SEQ ID NO:11:

(i) SEQUENCE CHARACTERISTICS:
            (A) LENGTH: 16 amino acids
            (B) TYPE: amino acid
            (C) STRANDEDNESS:
            (D) TOPOLOGY: linear
```

(ii) MOLECULE TYPE: peptide (xi) SEQUENCE DESCRIPTION: SEQ ID NO:11:

Asn Tyr Asn Val Leu Met Val Pro Lys Pro Gln Gly Pro Leu Pro Asn
1               5                  10                  15

(2) INFORMATION FOR SEQ ID NO:12:

(i) SEQUENCE CHARACTERISTICS:
           (A) LENGTH: 8 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:12:

Gly His Pro Leu Gln Lys Thr Tyr
1               5

(2) INFORMATION FOR SEQ ID NO:13:

(i) SEQUENCE CHARACTERISTICS:
           (A) LENGTH: 8 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:13:

Tyr Thr Lys Gln Leu Pro His Gly
1               5

(2) INFORMATION FOR SEQ ID NO:14:

(i) SEQUENCE CHARACTERISTICS:
           (A) LENGTH: 7 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:14:

Lys Pro Pro Lys Tyr His Pro
1               5

(2) INFORMATION FOR SEQ ID NO:15:

(i) SEQUENCE CHARACTERISTICS:
           (A) LENGTH: 8 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:15:

Phe Val Lys Arg Val Lys Thr Tyr
1               5

(2) INFORMATION FOR SEQ ID NO:16:

(i) SEQUENCE CHARACTERISTICS:
           (A) LENGTH: 7 amino acids
           (B) TYPE: amino acid
           (C) STRANDEDNESS:

```
            (D) TOPOLOGY: linear (ii) MOLECULE TYPE: peptide (xi) SEQUENCE DESCRIPTION: SEQ ID NO:16:

Leu Tyr Pro Gln His Lys Thr
1               5

(2) INFORMATION FOR SEQ ID NO:17:

(i) SEQUENCE CHARACTERISTICS:
            (A) LENGTH: 12 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:17:

Phe Gln Asp His Pro Leu Gln Lys Thr Tyr Asn Tyr
1               5                   10

(2) INFORMATION FOR SEQ ID NO:18:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:18:

Ala Pro Leu Gln Lys Thr Tyr
1               5

(2) INFORMATION FOR SEQ ID NO:19:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:19:

His Ala Leu Gln Lys Thr Tyr
1               5

(2) INFORMATION FOR SEQ ID NO:20:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:20:

His Pro Ala Gln Lys Thr Tyr
1               5

(2) INFORMATION FOR SEQ ID NO:21:

(i) SEQUENCE CHARACTERISTICS:
            (A) LENGTH: 7 amino acids
            (B) TYPE: amino acid
```

```
            (C) STRANDEDNESS:
            (D) TOPOLOGY: linear (ii) MOLECULE TYPE: peptide (xi) SEQUENCE DESCRIPTION: SEQ ID NO:21:

His Pro Leu Ala Lys Thr Tyr
1               5

(2) INFORMATION FOR SEQ ID NO:22:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:22:

His Pro Leu Gln Ala Thr Tyr
1               5

(2) INFORMATION FOR SEQ ID NO:23:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:23:

His Pro Leu Gln Lys Ala Tyr
1               5

(2) INFORMATION FOR SEQ ID NO:24:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:24:

His Pro Leu Gln Lys Thr Ala
1               5

(2) INFORMATION FOR SEQ ID NO:25:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:25:

His Pro Leu Gly Gln Lys Thr Tyr
1               5

(2) INFORMATION FOR SEQ ID NO:26:

(i) SEQUENCE CHARACTERISTICS:
            (A) LENGTH: 10 amino acids
```

```
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:26:

Phe Ser Phe Cys Glu Thr Asn Gly Leu Glu
1               5                   10

(2) INFORMATION FOR SEQ ID NO:27:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:27:

Phe Glu Thr Leu Gly Cys Asn Glu Gly Phe
1               5                   10

(2) INFORMATION FOR SEQ ID NO:28:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:28:

Phe Phe Ser Ala Thr Leu Gly Asn Glu Glu
1               5                   10

(2) INFORMATION FOR SEQ ID NO:29:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:29:

Ala Ser Phe Cys Glu Thr Asn Gly Leu Glu
1               5                   10

(2) INFORMATION FOR SEQ ID NO:30:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:30:

Phe Ala Phe Cys Glu Thr Asn Gly Leu Glu
1               5                   10

(2) INFORMATION FOR SEQ ID NO:31:

(i) SEQUENCE CHARACTERISTICS:
```

(A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

Phe Ser Ala Cys Glu Thr Asn Gly Leu Glu
1               5                   10

(2) INFORMATION FOR SEQ ID NO:32:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

Phe Ser Phe Ala Glu Thr Asn Gly Leu Glu
1               5                   10

(2) INFORMATION FOR SEQ ID NO:33:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:33:

Phe Ser Phe Cys Ala Thr Asn Gly Leu Glu
1               5                   10

(2) INFORMATION FOR SEQ ID NO:34:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:34:

Phe Ser Phe Cys Glu Ala Asn Gly Leu Glu
1               5                   10

(2) INFORMATION FOR SEQ ID NO:35:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:35:

Phe Ser Phe Cys Glu Thr Ala Gly Leu Glu
1               5                   10

(2) INFORMATION FOR SEQ ID NO:36:

(i) SEQUENCE CHARACTERISTICS:
    (A) LENGTH: 10 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:36:

```
Phe Ser Phe Cys Glu Thr Asn Ala Leu Glu
1               5                  10
```

(2) INFORMATION FOR SEQ ID NO:37:

(i) SEQUENCE CHARACTERISTICS:
    (A) LENGTH: 10 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:37:

```
Phe Ser Phe Cys Glu Thr Asn Gly Ala Glu
1               5                  10
```

(2) INFORMATION FOR SEQ ID NO:38:

(i) SEQUENCE CHARACTERISTICS:
    (A) LENGTH: 10 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:38:

```
Phe Ser Phe Cys Glu Thr Asn Gly Leu Ala
1               5                  10
```

(2) INFORMATION FOR SEQ ID NO:39:

(i) SEQUENCE CHARACTERISTICS:
    (A) LENGTH: 28 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:39:

```
Ala Ile Thr Phe Gly Gly Leu Leu Gly Glu Lys Thr Arg Asn Gln Met
1               5                  10                  15

Gly Val Ser Glu Leu Leu Ile Ser Thr Ala Val Gln
            20                  25
```

(2) INFORMATION FOR SEQ ID NO:40:

(i) SEQUENCE CHARACTERISTICS:
    (A) LENGTH: 28 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:40:

```
Val Phe Glu Glu Ala Phe Phe Ser Phe Cys Glu Thr Asn Gly Leu Glu
1               5                  10                  15
```

```
Tyr Ile Val Gly Arg Val Trp Ile Gly Phe Trp Leu
            20                  25
```

(2) INFORMATION FOR SEQ ID NO:41:

(i) SEQUENCE CHARACTERISTICS:
        (A) LENGTH: 58 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:41:

```
Thr Gln Glu Ile Phe Ser Phe Leu Ile Ser Leu Ile Phe Ile Tyr Glu
1               5                   10                  15
Thr Phe Ser Lys Leu Ile Lys Ile Phe Gln Asp His Pro Leu Gln Lys
            20                  25                  30
Thr Tyr Asn Tyr Asn Val Leu Met Val Pro Lys Pro Gln Gly Pro Leu
        35                  40                  45
Pro Asn Thr Ala Leu Leu Ser Leu Val Leu
    50                  55
```

(2) INFORMATION FOR SEQ ID NO:42:

(i) SEQUENCE CHARACTERISTICS:
        (A) LENGTH: 48 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:42:

```
Val Asp Phe Phe Ile Gln Asp Thr Tyr Thr Gln Lys Leu Ser Val Pro
1               5                   10                  15
Asp Gly Phe Lys Val Ser Asn Ser Ser Ala Arg Gly Trp Val Ile His
            20                  25                  30
Pro Leu Gly Leu Arg Ser Glu Phe Pro Ile Trp Met Met Phe Ala Ser
        35                  40                  45
```

(2) INFORMATION FOR SEQ ID NO:43:

(i) SEQUENCE CHARACTERISTICS:
        (A) LENGTH: 58 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:43:

```
Leu Ser Gly Ile Gln Leu Phe Asp Arg Ile Leu Leu Leu Phe Lys Pro
1               5                   10                  15
Pro Lys Tyr His Pro Asp Val Pro Tyr Val Lys Arg Val Lys Thr Trp
            20                  25                  30
Arg Met His Leu Phe Thr Gly Ile Gln Ile Ile Cys Leu Ala Val Leu
        35                  40                  45
Trp Val Val Lys Ser Thr Pro Ala Ser Leu
    50                  55
```

(2) INFORMATION FOR SEQ ID NO:44:

```
        (i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: one-of(1, 3)
            (D) OTHER INFORMATION: /product= "OTHER"
                /note= "Xaa = hydrophobic amino acid,
                e.g., Phe, Ala, Val, Leu or Ile"

(ix) FEATURE:
            (A) NAME/KEY: Modified-site
            (B) LOCATION: 2
            (D) OTHER INFORMATION: /product= "OTHER"
                /note= "Xaa = either hydrophobic amino
                acid, e.g., Phe, Ala, Leu or Ile, or
                unobstructive amino acid selected from
                the group consisting of Ala, Val, Leu,
                Ile, Met, Gly, Ser, Thr, Arg, Cys,
                Gln or Asn"

(ix) FEATURE:
            (A) NAME/KEY: Modified-site
            (B) LOCATION: one-of(4, 6, 7, 8, 9)
            (D) OTHER INFORMATION: /product= "OTHER"
                /note= "Xaa = unobstructive amino acid
                selected from the group consisting of
                Ala, Val, Leu, Ile, Met, Gly, Ser, Thr,
                Arg, Cys, Gln or Asn"

(ix) FEATURE:
            (A) NAME/KEY: Modified-site
            (B) LOCATION: one-of(5, 10)
            (D) OTHER INFORMATION: /product= "OTHER"
                /note= "Xaa = negatively charged amino
                acid, e.g., Glu or Asp"

(xi) SEQUENCE DESCRIPTION: SEQ ID NO:44:

Xaa Xaa Xaa Xaa Xaa Xaa Xaa Xaa Xaa Xaa
1               5                   10

(2) INFORMATION FOR SEQ ID NO:45:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /note= "Xaa = amino acid selected from
                the group consisting of Tyr, Phe or Ala"

(ix) FEATURE:
            (A) NAME/KEY: Modified-site
            (B) LOCATION: one-of(2, 4, 5, 6)
            (D) OTHER INFORMATION: /product= "OTHER"
                /note= "Xaa = unobstructive amino acid
                selected from the group consisting of
                Ala, Val, Leu, Ile, Met, Gly, Ser, Thr,
                Arg, Cys, Gln or Asn"

(ix) FEATURE:
            (A) NAME/KEY: Modified-site
            (B) LOCATION: 7
            (D) OTHER INFORMATION: /product= "OTHER"
```

-continued

/note= "Xaa = positively charged amino
acid, preferably Lys or His"

(xi) SEQUENCE DESCRIPTION: SEQ ID NO:45:

Xaa Xaa Lys Xaa Xaa Xaa Xaa
1               5

METHODS FOR ENHANCING THROMBOLYSIS IN A MAMMAL

CROSS REFERENCE TO RELATED APPLICATIONS

This application is related to U.S. patent application Ser. No. 08/405,647, filed Mar. 17, 1995.

STATEMENT REGARDING FEDERALLY SPONSORED RESEARCH

Not applicable.

FIELD OF THE INVENTION

The present invention relates to compositions and methods for use in enhancing thrombolysis in mammals.

BACKGROUND OF THE INVENTION

Formation of a blood clot (thrombus) in a blood vessel entails two principal events: platelet aggregation and deposition of fibrin. Within seconds of vessel injury, resting platelets become activated and are bound to the exposed surface of the injured area by a phenomenon called platelet adhesion. Activation of platelets also leads to enhanced binding of the surface adhesion molecule gpIIbIIIa (CD41), causing platelets to bind to each other in a process called platelet aggregation to form a platelet plug. Inhibitors of platelet activation, or of gpIIbIIIa activity, have been shown to prevent platelet aggregation and, hence, to reduce thrombus formation. The platelet plug can stop bleeding quickly, but it must be reinforced by fibrin for long-term effectiveness, until the vessel injury can be permanently repaired.

The coagulation system, involved in thrombus formation, has a natural counterpart in the fibrinolytic system. In the process of blood coagulation, a cascade of enzyme activities are involved in generating a fibrin network which forms the framework of a clot. Degradation of the fibrin network (fibrinolysis) is accomplished by the action of the enzyme plasmin. Plasminogen is the inactive precursor of plasmin and conversion of plasminogen to plasmin is accomplished by cleavage of the peptide bond between arginine 561 and valine 562 of plasminogen. Under physiological conditions this cleavage is catalysed by tissue-type plasminogen activator (tPA) or by urokinase-type plasminogen activator (uPA).

If the balance between the clotting and fibrinolytic systems becomes locally disturbed, intravascular clots may form at inappropriate locations leading to conditions such as coronary thrombosis and myocardial infarction, deep vein thrombosis, stroke, peripheral arterial occlusion and embolism. In such cases, the administration of fibrinolytic agents has been shown to be a beneficial therapy for the promotion of clot dissolution.

Fibrinolytic therapy has become relatively widespread with the availability of a number of plasminogen activators such as tPA, uPA, streptokinase and the anisoylated plasminogen streptokinase activator complex, APSAC. Each of these agents has been shown to promote clot lysis, but all have deficiencies in their activity profile which makes them less than ideal as therapeutic agents for the treatment of thrombosis (reviewed by Marder and Sherry, New England Journal of Medicine 1989, 318: 1513–1520). One of the major problems with tPA for the treatment of acute myocardial infarction or other thrombotic disorders is that it is rapidly cleared from the circulation with a plasma half-life in man of around 5 minutes (Bounameaux et al. in: "Contemporary Issues in Haemostasis and Thrombosis" vol 1 pp. 5–91, 1985. Collen et al. eds, Churchill Livingstone). This results in the need to administer tPA by infusion in large doses. The treatment is therefore expensive and is usually delayed since the patient has to be hospitalized before treatment can commence. Urokinase, in either the single chain form or the two chain form, has a similar rapid plasma clearance and also requires administration by continuous infusion.

A major problem shared by all of these agents is that at clinically useful doses, they are not thrombus specific as they activate plasminogen in the general circulation. The principal consequence of this is that proteins such as fibrinogen involved in blood clotting are destroyed and dangerous bleeding can occur. This also occurs with tPA despite the fact that, at physiological concentrations, it binds to fibrin and shows fibrin selective plasminogen activation. Significant efforts have been expended to find mutant or other forms of tPA and other fibrinolytic or thrombolytic agents with desirable activity, specificity, and duration.

Accordingly, a need exists in the art for additional agents which can enhance fibrinolysis. The subject invention fills this and other needs.

SUMMARY OF THE INVENTION

The subject invention discloses that agents which inhibit the interaction between the band 3 protein and its ligand (hereafter sometimes referred to as "interaction inhibitors" or "inhibitors"), CD36/thrombospondin, can also be used to enhance thrombolysis. The inhibitors can be peptides which contain sequences present in exofacial loops of the band 3 protein, or can be non-natural, D-isomer forms of the same sequences, or can be peptides, peptidomimetics, or non-peptidic molecules which interfere with band 3 protein—ligand interactions. One preferred group of such inhibitors comprises peptides characterized by the sequence motif $Z^2Z^3Z^2UX^-UUU\underline{U}X^-$ (SEQ ID NO:44), wherein $Z^2$ represents a hydrophobic residue, U represents unobstructive residues, $Z^3$ is either $Z^2$ or an unobstructive residue and $X^-$ represents negatively charged residues. Another preferred group of such inhibitors comprises peptides characterized by the sequence motif $Z^1UKUUUX^+$ (SEQ ID NO:45), wherein $Z^1$ is selected from the group consisting of tyrosine, phenylalanine and alanine; K is a lysine residue; U represents unobstructive residues; and $X^+$ is a positively charged residue. The reverse sequences of these peptides are also active. The inhibitors of the subject method can be administered alone or in combination with one or more additional therapeutic agents. Administration can be oral, intravenous or by other means, in amounts between about 0.1 mg/kg to about 20 mg/kg.

DETAILED DESCRIPTION OF THE INVENTION

I. Introduction

Figure 1:
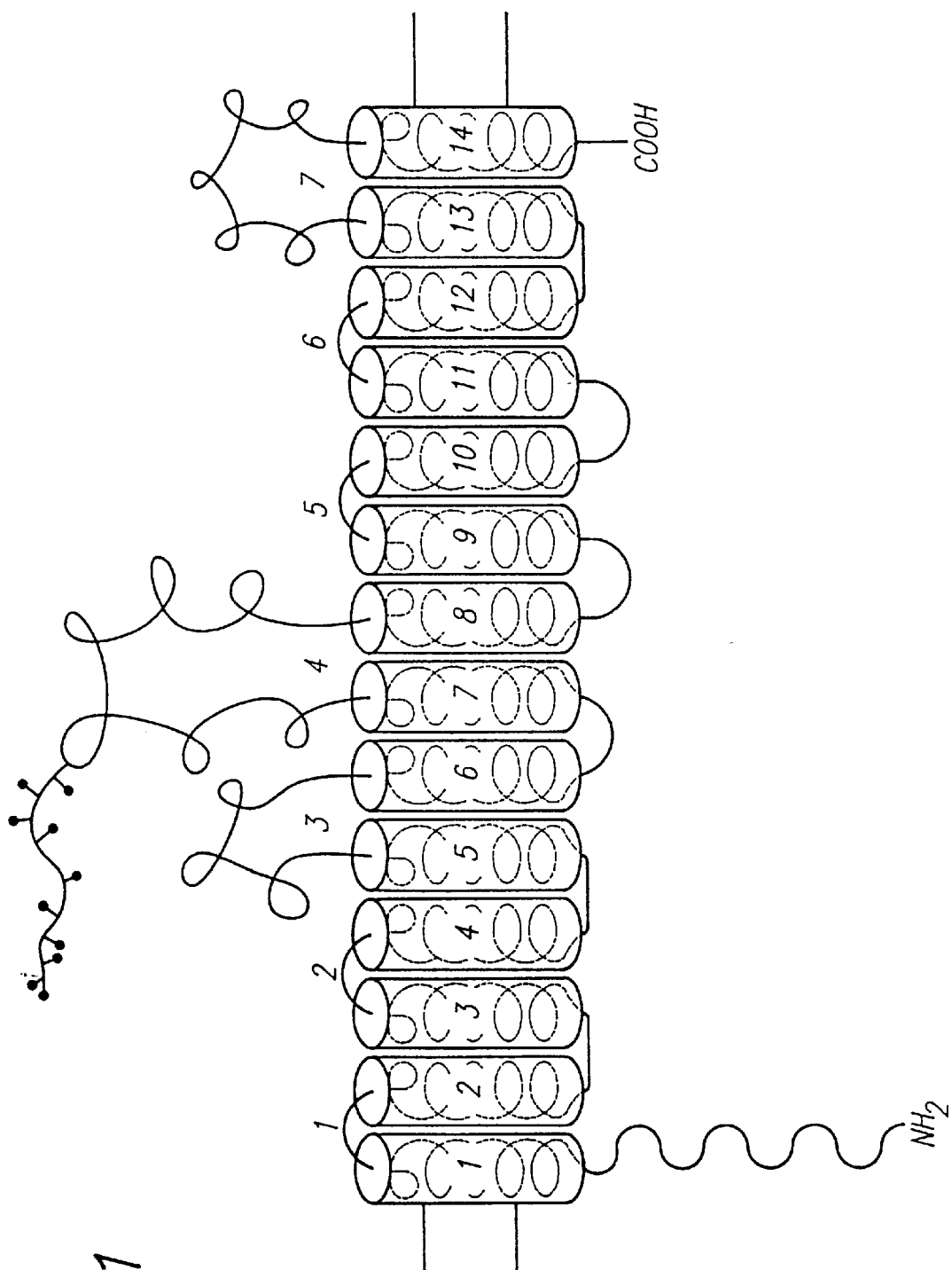
FIG. 1 illustrates the predicted secondary structure of band 3 protein by identifying regions of the band 3 molecule that are exofacial or membrane spanning. Division of amino acid sequences into external loop regions and membrane spanning regions is based on hydropathy plots and published amino acid sequence information.

It has recently been determined that the adhesiveness of red blood cells (hereafter sometimes referred to as RBCs or red cells) can be reduced by addition of peptides derived from a protein normally occurring on RBCs known as the band 3 protein, discussed in greater detail below. Initial studies on these peptides suggested that the ligand for the band 3 protein was the CD36 molecule. Subsequent studies have shown that thrombospondin is implicated as an intermediary in the interaction between the band 3 protein and the CD36 molecule. (Lucas, J. and Sherman, I., "*Plasmodium falciparum*: Thrombospondin mediates parasitized erythrocyte band 3-related adhesin binding", Expt'l. Parasitology (in press)). For convenience, the ligand for the band 3 protein will be referred to herein as CD36/thrombospondin.

It has now been found that inhibitors of the interaction between the band 3 protein and CD36/thrombospondin not only reduce cytoadhesiveness of red blood cells, but also leads to rapid lysis of a thrombus. Since thrombolysis involves the degradation of fibrin through the action of the protease plasmin, but is not known to involve the adhesion of red blood cells, this result could not have predicted from the prior findings on cytoadhesiveness.

As set forth in more detail below, a large number of inhibitors of the band 3 protein—ligand interaction are known, see International Patent Application No. WO96/29086, and sequence motifs have been shown for designing more. These inhibitors preferably are, but need not be, peptides or peptidomimetics.

Additionally, assays are now known for testing whether any particular molecule inhibits the band 3 protein—ligand interaction by determining the effect of the molecule on the adhesiveness of red blood cells. Two such assays are set forth below. Based on experimental results to date, it is expected that agents active as inhibitors of cytoadhesion in these assays will also function to enhance thrombolysis. Accordingly, these assays can now be used to test any compound for its effect in vivo as an anticytoadhesive and, hence, to determine its effect as an enhancer of thrombolysis.

After defining terms used herein, the discussion below sets forth information about the band 3 protein and on the development of inhibitors of the band 3-ligand interactions based on the initial work with peptide sequences present on extracellular portions of the protein. It then proceeds to explain how to make peptides, including peptidic inhibitors of the band 3 protein—ligand interaction, and uses of such inhibitors as enhancers of thrombolysis. It further discusses how to assay interaction inhibitors for activity as enhancers of thrombolysis and how to formulate and administer them as pharmaceutical compositions. Finally, it sets forth examples of assays and of use.

II. Definitions

For purposes of the present invention, the term "unobstructive residue" (U) is defined as an amino acid residue that does not interfere with the conformation of the peptide. Thus, U is selected from the group consisting of alanine (A), valine (V), leucine (L), isoleucine (I), methionine (M), glycine (G), serine (S), threonine (T), arginine (R), cysteine (C), glutamine (Q) and asparagine (N). Most preferably, the U residue in the human band 3 sequence is selected from the group consisting of valine (V), leucine (L), arginine (R), glutamine (Q), and threonine (T). Experimental evidence indicates that alanine (A) can be substituted for any U position. Substitution of a large amino acid residue (e.g., tyrosine, phenylalanine, tryptophan or histidine) or inappropriately charged amino acid residue (e.g., aspartic acid or glutamic acid) into a U position is expected to have a negative effect on the band 3 protein/CD36/throinbospondin interaction (e.g., the receptor/ligand interaction, further defined herein) and is therefore not preferred.

As used herein, "fibrinolysis" is intended to encompass the process by which fibrin clots are dissolved.

As used herein, "thrombolysis" means the resolution or prevention of platelet aggregation within the vascular bed and the dissolution of blood clots through fibrinolysis. It is therefore a more encompassing term than is fibrinolysis.

The terms "enhance" or "enhancing" with regard to thrombolysis mean a statistically meaningful, detectable decrease of the time required (1) in an in vitro use, to lyse a sample of clotted blood, or (2) in an in vivo use, for the restoration of blood flow in a vessel, in comparison to an untreated control. The body maintains a balance between the coagulation system for clotting blood, where needed, and the fibrinolytic system for dissolving clots once they are formed. Because the body maintains a balance between these systems, agents which enhance coagulation usually cause an increase in the rate of fibrinolysis. Agents which increase coagulation are therefore considered herein to enhance fibrinolysis if an increase in fibrinolysis results. "Inhibitor of band 3 protein—ligand interaction," and "interaction inhibitor" and "inhibitor" as used herein mean a compound which can compete, competitively or non-competitively, with the interaction between an anion transporter protein found in the membrane of red blood cells and known in the art as the band 3 protein, thrombospondin, and CD36 (as noted in the Introduction section, above, it is now known that thrombospondin acts as an intermediary in the interaction of the band 3 protein and CD36).

As used herein, the terms "band 3 protein," "protein band 3," and "band 3" are synonymous terms designating an anion transporter protein found in the membrane of red blood cells and known in the art as the band 3 protein.

The terms "loop 2 peptide" and "loop 3 peptide" refer to peptides derived from protein sequences present in, respectively, extracellular loop (or "exofacial") domains 2 and 3 of the band 3 protein as determined by hydropathy plots and published amino acid sequence information [Tanner et al., *Biochem. J*. 256:703–12 (1988)]. FIG. 1 is a representation of the band 3 protein depicting the extracellular loops, including loops 2 and 3.

"Conservative substitution" means the replacement of an amino acid residue with a functionally similar residue. Examples of conservative substitutions include the substitution of the substitution of one polar (hydrophilic) residue for another such as between arginine and lysine, between glutamine and asparagine, between glycine and serine, the substitution of one basic residue such as lysine, arginine or histidine for another, the substitution of one acidic residue, such as aspartic acid or glutamic acid for another, or the substitution of one non-polar (hydrophobic) residue such as isoleucine, valine, leucine or methionine for another. References to amino acids as "basic" or "acidic" refer to their ionic charge at physiological pH.

"Substantially identical," as used herein in the context of a subject peptide sequence, means that when the subject sequence is maximally aligned with a reference peptide sequence, there is a 90% or greater identity taking into account conservative substitutions in the subject peptide sequence of amino acids present in the reference sequence, the net effect of which does not result in an adverse functional dissimilarity between reference and subject sequences.

References to an amino acid as "negatively" or "positively" charged refer to the overall ionic charge of that amino acid at physiological pH.

References to an amino acid as "hydrophobic" refer to amino acids with larger aliphatic side groups or aromatic side groups which tend to be averse to exposure to water and to cluster together.

By "administered in combination" or "combination therapy" it is meant that the inhibitors of the invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a protein gives rise to essentially one band in an electrophoretic gel. Particularly, it means that the protein is at least 85% pure, more preferably at least 95% pure, and most preferably at least 99% pure.

A "peptide" or "polypeptide" of the present invention comprises no more than about 100 amino acid residues, preferably no more than about 50 residues, more preferably no more than about 20 residues, and most preferably about 12 or fewer amino acids, and includes an amino acid residue sequence defining a band 3—ligand interaction inhibitor, as described herein.

"Reverse sequence" (or "reverse of a sequence") means a sequence which is in the reverse order of a referenced amino acid sequence. For example, the sequence YTKQLPHG [SEQ ID NO:13] is the reverse sequence of the sequence GHPLQKTY [SEQ ID NO:12]. As noted in a succeeding section, reverse sequences of the peptides taught herein as reducing adhesion in cytoadhesion assays were themselves able to reduce adhesion in such assays; they are accordingly intended to be encompassed within the scope of the claimed methods.

"Sequence motif" refers to a sequence defining the type of amino acid residues which can be in particular positions in a peptide by relation to the types of residues around those positions. For example, a sequence motif "X⁻WX⁺" requires that a negatively charged amino acid and a positively charged amino acid flank the "W" (tryptophan, following the convention for single-letter symbols for amino acids) amino acid.

Unless otherwise indicated, amino acid sequences are written left to right in amino to carboxy orientation. Numeric ranges are inclusive of the numbers defining the range.

III. The Band 3 Protein

Band 3 is an anion transporter protein found in the cell membrane of red blood cells, having transmembrane regions and exofacial "loop" regions. Band 3 protein is present in approximately one million copies per red cell in the form of monomers, dimers, or tetramers. The band 3 monomer has a molecular weight of approximately 95 kDa, with two distinct domains: a 43 kDa water-soluble cytoplasmic domain, and a 55 kDa membrane-spanning domain (Low, *Biochimica et Biophyzica Acta* 864:145–167 (1986)). The gene for band 3 protein has been cloned and sequenced (Tanner et al., *Biochem. J.* 256:703–12 (1988); Lux et al., *Proc. Nat'l. Acad. Sci. USA* 86:9089–93 (1989)).

From the published amino acid and nucleotide sequences, information about the hydrophobicity and hydrophilicity of amino acids in the sequence, and observed features of the protein (e.g., flexibility of protein segments, reactivity of residues in intact cell), it is possible to derive a working two-dimensional profile of band 3. FIG. 1 illustrates a prediction of the regions of the band 3 molecule that are exofacial or membrane spanning. Division of sequences into external loop regions is based on hydropathy plots and published amino acid sequence information (Tanner et al., supra, Lux et al., supra). For example, exofacial loop 2 is located between amino acids 478–490, loop 3 is located between amino acids 539–569, and loop 7 is located between amino acids 815 and 851. Reference is made herein to amino acid residue numbers based on the published sequence of the band 3 protein, thereby relating peptides of the invention to the band 3 protein and gene.

IV. Inhibitors of Band 3 Protein—Ligand Interactions a. Introduction

This invention involves the use of inhibitors of band 3 protein—ligand interactions to enhance thrombolysis. Many inhibitors of the band 3 protein—ligand interaction are derived from sequence motifs found in the exofacial loops of the band 3 protein. But the invention is not limited to these compounds. Using the adhesiveness assays and assays for determining clot lysis time, platelet aggregation, and other measures of thrombolytic activity described within, one can readily identify and test other compounds as inhibitors of band 3 protein—ligand interactions.

Initial work on such inhibitors commenced with a study of exofacial regions of band 3 protein. Predicted exofacial regions of band 3 protein (Table 1 and FIG. 1) were based on published data and used as the pattern for overlapping decapeptides. All peptides were patterned on the reported human band 3 amino acid sequences (Lux et al., supra; Tanner et al., supra).

Regions of interest are indicated in Table 1 below. Hydrophobic regions are indicated by an underline while regions with average access values of 4 or greater are indicated in bold face. Start residues of peptides with an average reactivity greater than 1.0 are marked with a dot above the residue. Hydrophobicity and access predictions indicated in Table 1 are based on a moving average value for nine amino acids (i.e., the indicated residue, four residues upstream and four residues downstream) where a negative value for the average hydrophobicity values is considered to constitute a hydrophobic region and an average access value of 4 or greater is considered to be an accessible region (Parker et al,. *Biochem.* 25:5425–5432 (1986)). Regions with low hydrophilicity and access values are predicted to be transmembranous.

TABLE 1

| Putative exofacial region | Residue numbers | Sequence | SEQ ID NO. |
|---|---|---|---|
| loop 1 | 420–447 | AIT<u>FGGLL</u>GEKTRNQMG<u>VSELLISTAVQ</u> | 39 |
| loop 2 | 470–497 | VFEEAFFSFCETNG<u>LEYIVGRVWIGFWL</u> | 40 |
| loop 3 | 520–577 | TQ<u>EIFSFLISLIFIY</u>ETFS<u>KLIK</u>IFQDHPL <u>.......</u> QKTYN<u>Y</u>NVLMVPKPQGPLPNT<u>ALLSLVL</u> | 41 |
| loop 4 | 620–667 | V<u>DFF</u>IQDTYTQKLSVPDGFKVSNSSARGW<u>V</u> <u>..</u> <u>IHP</u>LGLRSEF<u>PIWMMFAS</u> | 42 |
| loop 7 | 800–857 | LSGI<u>QLFDRILLL</u>FKPPKYHPDVPYVKRVK <u>..</u> TWR<u>MHLFTGIQIICLAVLWVV</u>KSTPASL | 43 | b. Loop 3 peptides

A first group of inhibitors of band 3 protein—ligand—interaction is characterized by a loop 3 sequence motif, $Z^1UKUUUX^+$ (SEQ ID NO:45) In this motif, $Z^1$ is selected from the group consisting of tyrosine, phenylalanine and alanine (preferably, tyrosine or phenylalanine); K is a lysine residue; U is an unobstructive residue as defined above; and $X^+$ is a positively charged residue (preferably a lysine or a histidine residue). One preferred embodiment, peptide GHPLQKTY (SEQ ID NO:12) represents residues 546–553 from band 3 protein exofacial loop 3. Additional peptides with the substitutions described below are also preferred embodiments.

Alanine substitution experiments, using cytoadhesion assays, indicated that alanine is tolerated in the $Z^1$ residue position, an observation consistent with previous observations (e.g., iodination of the peptides results in incorporation of iodine atoms into tyrosine residues which abolishes peptide-blocking activity and suggests that the Z residue participates in a hydrophobic interaction with the receptor, CD36). The advantage of the presence of the preferred $Z^1$ group tyrosine or phenylalanine can be inferred from the following observations: (1) Two active forms of the peptide (HPLQKTY (SEQ ID NO:1) and YVKRVK (SEQ ID NO:2)) contain a tyrosine residue in the same relative position; and (2) The peptide YVK (SEQ ID NO:3) has an $IC_{50}$ that is 1/1000 that of lysine (K) alone.

The presence of unobstructive ("U") residues is necessary since the spacing between the K residue and the U residue is important to the cytoadhesion activity of the peptide. For example, the shortened peptide HPQKTY (SEQ ID NO:4) is inactive, whereas the lengthened peptide HPLGQKTY (SEQ ID NO:5) retains its activity. The U residue is a lysine in the sequence YVKRVK (SEQ ID NO:25) and a protonated histidine residue in the sequence HPLQKTY (SEQ ID NO:1). Latex microspheres coated with one or the other of these sequences indicate that the sequence HPLQKTY (SEQ ID NO:1) displays pH dependency (as observed in an infected erythrocyte/CD36 interaction) while the sequence YVKRVK (SEQ ID NO:2) does not. Microsphere studies indicate that the peptide HPLQKTY (SEQ ID NO:1) has a higher affinity for CD36 than YVKRVK ((SEQ ID NO:2). Overlapping peptides with the above identified motif are shown in Table 2.

TABLE 2

| Peptide | Sequence | Comment | SEQ ID NO: |
|---|---|---|---|
| 3a | DHPLQKTYNY | residues 546–555 | 6 |
| 4 | YTQKLSVPDGFKVSN | residues 628–642 | 7 |
| 3b | KLIKIFQPHPQKTY | residues 539–553 | 8 |
| 7a | KPPKYHPDVPYVKR | residues 814–827 | 9 |
| 7b | DVPYVKRVKTWRMH | residues 821–834 | 10 |
| 3c | NYNVLMVPKPQGPLPN | residues 554–569 | 11 |
| 7c | YVKRVK | residues 824–829 | 2 |
| 3d | GHPLQKTY | residues 546–553 | 12 |
| 7d | YVK | residues 824–826 | 3 |
| 3e | YTKQLPHG | residues 553–546 | 13 |
| 7e | KPPKYHP | residues 814–820 | 14 |
| — | FVKRVKTY | based on residues 824–829 | 15 |
| 3ds | LYPQHKT | scramble of residues 547–553 | 16 |
| 3d(D) | GHPLQKTY | synthesized with D amino acids; residues 546–553 | "—" |
| 3f | FQDHPLQKTYNY | residues 544–555 | 17 |
| — | APLQKTY | alanine substitution based on 547–553 | 18 |
| — | HALQKTY | alanine substitution based on 547–553 | 19 |
| — | HPAQKTY | alanine substitution based on residues 547–553 | 20 |
| — | HPLAKTY | alanine substitution based on residues 547–553 | 21 |
| — | HPLQATY | alanine substitution based on residues 547–553 | 22 |
| — | HPLQKAY | alanine substitution based on residues 547–553 | 23 |
| — | HPLQKTA | alanine substitution based on residues 547–553 | 24 |
|  | HPLGQKTY | length altered | 25 |
| — | HPQKTY | length altered | 4 |

The peptide backbone appears to play little part in the activity of the peptide since the order of the residues can be reversed (i.e., GHPLQKTY (SEQ ID NO:12) is as active as YTKQLPHG (SEQ ID NO:13)) and the L-amino acid and D-amino acid forms of the peptide GHPLQKTY (SEQ ID NO:12) have equal activity. In these sequences, a G residue is added to both peptides for synthetic considerations.

c. Loop 2 peptides

A second group of inhibitors of the band 3 protein—ligand interaction is characterized by a loop 2 sequence motif, $Z^2Z^3Z^2UX^-UUU\underline{U}X^-$ (SEQ ID NO:44), wherein $Z^2$ represents a hydrophobic residue (phenylalanine (F), alanine (A), valine (V), leucine (L), or isoleucine (I)) (preferably, phenylalanine); U represents an unobstructive residue as defined above; $Z^3$ is either $Z^2$ or U; and $X^-$ represents a negatively charged residue (e.g., glutamic acid (E) or aspartic acid (D)). A preferred embodiment is peptide FSFCETNGLE (SEQ ID NO:26), amino acid residues 476–485 of band 3 protein exofacial loop 2. Additional peptides with the substitutions described below are also preferred embodiments.

Identification of this motif was based in part on the observation that the tyrosine in pfalhesin participated in a hydrophobic interaction, which did not tolerate the presence an iodine atom, and that two negative charges should be spaced in such a way that they could interact with the lysine and histidine residues of pfalhesin. Cytoadherence assays indicated that anti-band 3 mouse monoclonal 5H12 had properties inconsistent with non-competitive inhibition of the pfalhesin/CD36/thrombospondin interaction. PEPSCAN analysis indicated that the epitope of the antibody was FSFCETNGLE (SEQ ID NO:26), a motif that can be abbreviated to $Z^2UZ^2UX^-UUUUX^-$ (SEQ ID NO:5), where $Z^2$, U and $X^-$ are defined as above, a close approximation of the motif predicted to form the receptor domain of pfalhesin.

Attempts to produce an inactive scramble of the sequence FSFCETNGLE (SEQ ID NO:26) based on residues 476–485 of band 3 led to the production of control peptides FETLGCNEGF (SEQ ID NO:27) and FFSATLGNEE (SEQ ID NO:28). Alanine substitution experiments, using cytoadhesion assays and employing the peptides ASFCETNGLE (SEQ ID NO:29), FAFCETNGLE (SEQ ID NO:30), FSACETNGLE (SEQ ID NO:31), FSFAETNGLE (SEQ ID NO:32), FSFCATNGLE (SEQ ID NO:33), FSFCEANGLE (SEQ ID NO:34), FSFCETAGLE (SEQ ID NO:35), FSFCETNALE (SEQ ID NO:36), FSFCETNGAE (SEQ ID NO:37) and FSFCETNGLA (SEQ ID NO:38), confirmed that both glutamic acid residues (E) are important to the peptide's cytoadhesion activity.

Finally, in limited studies of single substituted isomers (that is, where one residue is of the D-isomer and the rest of the residues are L-isomers, and vice versa), it was found that mixed isomers were inactive in cytoadhesion assays. However, it remains to be seen whether other combinations of L- and D- isomers would retain activity.

V. Peptide Synthesis a. Solid phase synthesis

Peptides can be prepared by classical methods known in the art, for example, by using standard solid phase techniques. The standard methods include exclusive solid phase synthesis, partial solid phase synthesis methods, fragment condensation, classical solution synthesis, and recombinant DNA technology (see, e.g., Merrifield, *J. Am. Chem. Soc.* 85:2149 (1963)).

For example, peptides can be synthesized using the following solid phase methodology. In solid phase techniques, the synthesis is typically commenced from the C-terminal end of the peptide using an alpha-amino protected resin. A suitable starting material can be prepared, for instance, by attaching the required alpha-amino acid to a chloromethylated resin, a hydroxymethyl resin, or a benzhydrylamine resin. One such chloromethylated resin is sold under the tradename BIO-BEADS SX-1 by Bio Rad Laboratories, Richmond, Calif., and the preparation of the hydroxymethyl resin is described by Bodonszky et al., *Chem. Ind.* 38:1597 (1966).

Thus, peptides with the desired inhibition of the band 3 protein—ligand—interaction can be prepared by coupling an alpha-amino protected amino acid to the chloromethylated resin with the aid of, for example, cesium bicarbonate catalyst, according to the method described by Gisin, *Helv. Chim. Acta* 56:1467 (1973). After the initial coupling, the alpha-amino protecting group is removed by a choice of reagents including trifluoroacetic acid (TFA) or hydrochloric acid (HCl) solutions in organic solvents at room temperature.

The alpha-amino protecting groups are those known to be useful in the art of stepwise synthesis of peptides. Included are acyl type protecting groups (e.g., formyl, trifluoroacetyl, acetyl), aromatic urethane type protecting groups (e.g., benzyloxycarboyl (Cbz) and substituted Cbz), aliphatic urethane protecting groups (e.g., t-butyloxycarbonyl (Boc), isopropyloxycarbonyl, cyclohexyloxycarbonyl) and alkyl type protecting groups (e.g., benzyl, triphenylmethyl). Boc, tboc, and Fmoc are preferred protecting groups. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

The side chain protecting groups for Tyr include tetrahydropyranyl, tert-butyl, trityl, benzyl, Cbz, Z-Br-Cbz, and 2,5-dichlorobenzyl. The side chain protecting groups for Asp include benzyl, 2,6-dichlorobenzyl, methyl, ethyl, and cyclohexyl. The side chain protecting groups for Thr and Ser include acetyl, benzoyl, trityl, tetrahydropyranyl, benzyl, 2,6-dichlorobenzyl, and Cbz. The side chain protecting group for Thr and Ser is benzyl. The side chain protecting groups for Arg include nitro, Tosyl (Tos), Cbz, adainantyloxycarbonyl mesitoylsulfonyl (Mts), or Boc. The side chain protecting groups for Lys include Cbz, 2-chlorobenzyloxycarbonyl (2-Cl-Cbz), 2-bromobenzyloxycarbonyl (2-BrCbz), Tos, or Boc.

After removal of the alpha-amino protecting group, the remaining protected amino acids are coupled stepwise in the desired order. An excess of each protected amino acid is generally used with an appropriate carboxyl group activator such as dicyclohexylcarbodiimide (DCC) in solution, for example, in methylene chloride ($CH_2Cl_2$), dimethyl formamide (DMF) mixtures.

After the desired amino acid sequence has been completed, the desired peptide is decoupled from the resin support by treatment with a reagent such as trifluoroacetic acid or hydrogen fluoride (HF), which not only cleaves the peptide from the resin, but also cleaves all remaining side chain protecting groups. When the chloromethylated resin is used, hydrogen fluoride treatment results in the formation of the free peptide acids. When the benzhydrylamine resin is used, hydrogen fluoride treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides. These solid phase peptide synthesis procedures are well known in the art and further described in Stewart, *Solid Phase Peptide Syntheses* (1969).

b. Synthetic amino acids

The procedures can also be used to synthesize peptides in which amino acids other than the 20 naturally occurring, genetically encoded amino acids are substituted at one, two, or more positions of any of the compounds of the invention.

For instance, naphthylalanine can be substituted for tryptophan, facilitating synthesis. Other synthetic amino acids that can be substituted into the peptides of the present invention include L-hydroxypropyl, L-3,4-dihydroxyphenylalanyl, and isoquinolyl. In one preferred embodiment, D-amino acids are incorporated into the peptides of the present invention. In some preferred embodiments, sequences comprising only D-amino acids are employed.

One can replace the naturally occurring side chains of the 20 genetically encoded amino acids (or D-amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered hetereocyclic. For example, proline analogs in which the ring size of the proline residue is changed from 5 members to 4, 6, or 7 members can be employed. Cyclic groups can be saturated or unsaturated, and if unsaturated, can be aromatic or non-aromatic.

Cyclic groups can be saturated or unsaturated, and if unsaturated, can be aromatic or non-aromatic. Heterocyclic groups preferably contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (e.g., morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. These heterocyclic groups can be substituted or unsubstituted. Where a group is substituted, the substituent can be alkyl, alkoxy, halogen, oxygen, or substituted or unsubstituted phenyl.

One can also readily modify peptides of the instant invention by phosphorylation, or other methods for making peptide derivatives of the compounds of the present invention. Thus, peptide compounds of the invention also serve as a basis to prepare peptide mimetics with similar biological activity.

For purposes of the present invention, the term "peptide" refers to compounds comprising about 50 amino acids or less; preferably, the peptides of the present invention comprise less than about 25 amino acids, more preferably less than about 20 amino acids and most preferably about 10–12 or fewer amino acids. Hybrid proteins with suitable properties combining the sequences of the present invention with another protein may also be employed in accordance with the present invention; such hybrid proteins may be suitably prepared using, e.g., recombinant DNA techniques well known to those of skill in the art.

While reference is made to peptides herein, it is not necessary that the compounds comprise only peptides in a form corresponding to fragments of naturally—occurring proteins. To the extent that a compound contains the requisite sequence and meets the other criteria specified herein, modifications and substitutions in peptide structure currently known to those skilled in the art or which may hereinafter be developed are contemplated as within the scope of the present invention.

VI. Cytoadhesion and the Band 3 Protein

The band 3 protein has been established as playing a key role in cytoadhesion in at least two major diseases (malaria and sickle cell disease) affecting red blood cells. See, International Patent Application WO 96/29086. Modifications in band 3 occur in a number of otherwise-unrelated conditions (e.g., malaria, sickle cell disease, thalassemia, diabetes) such that there is clustering and a change in the conformation of this protein which exposes normally cryptic adhesive sites. Due to this change in protein conformation and exposure, erthyrocytes, which are normally non-adherent, develop adhesiveness to endothelial tissues.

Several of the inhibitors employed in accordance with the present invention were first identified in the course of examination of the properties of malaria-infected erythrocytes. A number of in vitro red cell adhesion models for malarial sequestration using umbilical vein endothelial cells and amelanotic melanoma cells have been described (Udeinya et al., *Science* 213:555–557 (1981); Schmidt et al., *J. Clin. Inv.* 70:379–386 (1982)). These in vitro systems were used to search for the molecule on the surface of the *P. falciparum*-infected red cell that mediated adhesion.

In a search for this putative adhesin, murine monoclonal antibodies (Mabs) against live *P. falciparum*-infected red cells were prepared (Winograd et al., *J. Cell Biol.* 108:23–30 (1989); Crandall et al., *Parasitology* 102:335–340 (1991)). These Mabs recognized only red cells bearing mature stages of *P. falciparum*, and did not react with uninfected, aged, or ring-infected red cells. Several of these Mabs blocked cytoadherence in a dose-dependent manner. Since none of these Mabs reacted with the intracellular parasite or immunoprecipitated parasite-encoded proteins, it appeared that the antigen was related to a membrane protein of the red cell. By peptide mapping of the antigens immunoprecipitated by these Mabs from surface iodinated red cells, it was possible to show that the infected red cell antigens were homologous to band 3 protein.

Using the anti-*P. falciparum* and anti-band 3 Mabs with unsealed and sealed red cells, it was possible to localize the epitopes of band 3 that were recognized by the adherence-blocking Mabs. The epitopes corresponded to putative exofacial loops 3 and 7 of the band 3 protein, but not loop 4 (which contains the sugar).

Several synthetic peptides corresponding to these epitopes were tested for their ability to inhibit the adherence of *P. falciparum*-infected red cells. Active peptides with $IC_{50}$ values in the micromolar range contained the sequences: HPLQKTY (SEQ ID NO:1) and YVKRVK (SEQ ID NO:2) (Crandall et al., *Proc. Natl. Acad. Sci. USA* 90:4703–4707 (1993)). These peptides were named pfalhesin (for *P. falciparum* adhesin).

Murine monoclonal, primate, and rabbit polyclonal sera prepared against synthetic pfalhesin reacted only with the surface of infected red cells bearing mature stage parasites (and not uninfected or ring-infected red cells). In addition, the antibodies blocked the adherence of these cells in a dose dependent manner (Crandall et al., *Parasitology* 108:389–396 (1994)). These findings indicated that exposure of cryptic residues of band 3 was responsible for the adhesiveness of *P. falciparum*-infected red cells. A murine monoclonal antibody (Mab) generated against synthetic peptides composed of amino acids 542–555 of human band 3 recognized only infected red cells and blocked their adherence, whereas another Mab generated against intact band 3, which recognized this same amino acid sequence, recognized all red cells and did not block the adherence of infected cells. These results demonstrated that Mabs reactive with a common amino acid sequence may bind to different conformations of that sequence, and suggested that the adherence of *P. falciparum*-infected red cells may result from a change in the surface topography of the band 3 protein.

Knowledge of the red cell adhesin in *P. falciparum*-infected red cells also permitted identification of the pfalhesin receptor on the target endothelial cell. Using Chinese hamster ovary (CHO) cells transfected with genes encoding for either ICAM-1 or CD36, it was shown that pfalhesin and CD36 formed a ligand/receptor pair. CD36-mediated adherence was non-competitively inhibited by monoclonal antibodies both to synthetic band 3 peptides and to live *P. falciparum*-infected red cells, and was competitively inhibited by pfalhesin. Immobilized pfalhesin, when used as an affinity matrix, purified only CD36 from cell extracts (Crandall et al., *Experimental Parasitology* 75:203–209 (1994)). The primary event in adhesion therefore appears to involve the binding of a band 3 derived "adhesin" localized on the surface of the red blood cell to at least one of its endothelial receptors, CD36/thrombospondin.

Pfalhesin was active as an inhibitor of cytoadhesion both in vitro and in vivo in Saimiri and Aotus monkeys, whereas a peptide with a scrambled array of amino acids was without effect. Strikingly, in the in vivo studies, when infected monkeys were treated with micromolar intravenous pfalhesin, a tide of infected red cells was released from sequestration sites into the peripheral circulation (Crandall et al., supra). Both the L- and D- forms of the pfalhesin peptides effectively inhibited adhesion.

The adhesion of sickle red cells to the vascular endothelium is likely critical to the initiation or amplification of the episodic vaso-occlusive events of sickle cell disease. The early pathologic lesions found in the lungs of a mildly hypoxic SAD mouse model of sickle cell disease show early unorganized thrombi composed of sickle cells, platelet aggregates, and fibrin deposits precisely consistent with this scenario. In addition, in a study using the ex vivo mesocecum vasculature of the rat (Katil et al., *Proc. Natl. Acad. Sci. USA* 86:3356–3360 (1989)), a single bolus of washed oxy-normal erythrocytes or oxy-sickle cells (unseparated or density-defined sickle cell classes) was infused, and by hemodynamic monitoring and intravital microscopic observations of the microvascular flow, higher peripheral resistance for sickle erythrocytes and adherence of these cells exclusively to the venular endothelium, but rare or no adherence of oxy-normal cells, were revealed. Both of these models can therefore be used to test the in vivo efficacy of synthetic peptides in remediating the microvascular adhesion of red cells.

VII. Uses in Enhancing Thrombolysis

Inhibitors of band 3—ligand interactions are useful to enhance fibrinolytic or thrombolytic activity. The small peptide and peptidomimetic interaction inhibitors are expected to be particularly useful. Small peptides and peptidomimetics can be taken orally and are promptly available because of rapid absorption. They are therefore expected to be preferred to agents (such as tPA) which require i.v. or other parenteral administration, particularly in non-hospital settings. For example, patients at high risk for a heart attack can be given tablets or capsules containing the peptides and or peptidomimetics, in a formulation permitting quick dissolution, to take orally at home at the first onset of a heart attack.

Peptide, peptidomimetic, and non-peptide inhibitors of band 3-ligand interaction are also expected to be useful:

(1) in the management of acute myocardial infarction, for the lysis of intracoronary thrombi, the improvement of ventricular function, and reduction of congestive heart failure, and reduction of mortality;
(2) for the lysis of pulmonary emboli blocking blood flow to one or more lobes of the lung;
(3) for the lysis of acute arterial thrombosis and embolism;
(4) for the lysis of thrombosis in deep veins or in cerebral sinuses (large blood vessels which drain cerebral blood back towards the heart);
(5) to reopen i.v. catheters obstructed by clotted blood or fibrin, and,
(6) in preventing clot formation or lysing clots as they form in devices such as heart lung machines and kidney dialysis machines in which blood is removed from the body and circulated before reinfusion;
(7) to prevent clotting in blood samples drawn from patients for clinical testing; and
(8) to prevent the recurrence of thrombosis in patients by prophylactic administration.

Administration of fibrinolytic agents is contraindicated in situations where the risk due to uncontrolled bleeding is greater than the potential benefit to the patient of dissolution of the thrombosis or embolism. Such situations are well known to medical and veterinary practitioners and include active internal bleeding, hemorrhagic stroke or intracranial or intraspinal surgery, intracranial neoplasm, and other situations in which bleeding would constitute a significant hazard or would be difficult to control due to its location.

VIII. Assays for Enhancement of Thrombolytic Activity

A number of assays are known in the art for measuring thrombolysis and components of the thrombolytic system. For example, U.S. Pat. No. 5,612,187 provides a clot time determining device and method for determining the time necessary for a test fluid to lyse a clot. This test can provide a measure of the action of plasminogen activators and plasmin in the blood. The patent further contains a discussion on the complex interplay between and balance of the coagulation system, which when working properly forms clots to protect the body from loss of blood, and the fibrinolytic system, which when working properly removes clots when they are no longer needed. The patent further refers to commercially available kits for immunologic detection of fibrin degradation products, permitting a measure of the function of the fibrinolytic system. U.S. Pat. No. 5,587,159 teaches assays for fibrinolytic activity and plasminogen activation, as well as direct and indirect assays for plasmin formation.

Use of thrombolytics affects the clotting time of blood in a patient during and for some time after the administration of the agent. It is currently recommended that where time permits, the use of such agents be preceded by obtaining a hematocrit, platelet count, a thrombin time (TT), activated partial thromboplastin time (APTT), or prothrombin time. Coagulation tests and measures of fibrinolytic activity can be made during the administration of the agents if desired. All of these tests are known in the art.

For example, coagulation assay procedures are described, in Smith, et al., Thrombosis Research, 50: 163–174 (1988). U.S. Pat. Nos. 5,688,813 and 5,668,289 teach assaying coagulation time and related determinations in murine and canine models of arterial injury and of coronary artery thrombosis. U.S. Pat. Nos. 4,861,712; 4,910,510; 5,059,525; and 5,580,744 describe test articles suitable for monitoring blood coagulation. U.S. Pat. No. 4,756,884 describes a capillary flow device for measuring blood characteristics, including prothrombin time. A platelet aggregation assay, a platelet-fibrinogen binding assay, and a thrombolytic assay, are all taught in U.S. Pat. No. 5,661,159. Simple tests, such as rocking a blood sample in a test tube and timing the period until the blood clots, in the presence or absence of known or potential anti-coagulants, are also known.

With regard to measuring fibrinolytic activity, the following assays are noted as examples of available techniques. Plasminogenolytic activities can be measured using the Spectrolyse Tissue Plasminogen Activator Activity and Inhibitor Assay kit (American Diagnostica, Greenwich, Conn., Catalog #452). Reactions can be monitored by a ThermoMax™ plate reader (Molecular Devices, Palo Alto, Calif.) and SoftMax™ software.

The ability of inhibitors of band 3 protein—ligand interactions to lyse clots can be measured using a modification of the microtiter plate method described by Beebe et al., 1987, Thrombosis Res. 47:123–128. Fifty $\mu$l of assayed human reference plasma (Helena Laboratories) is mixed with 50 $\mu$l of APTT reagent (Helena Laboratories) and 30 $\mu$l of various concentrations of the interaction inhibitors in a buffer consisting of 0.001N HCl, 0.011% Tween 80, 50 mM Tris (pH 8.0), and 250 mM NaCl. The mixture is incubated for 5 minutes at 37° C. Clot formation is initiated by addition of 25 $\mu$l of 100 mM $CaCl_2$. The formation and subsequent dissolution of the clot are monitored by a ThermoMax™ plate reader (Molecular Devices) and SoftMax™ software. Rates of clot lysis are determined from the slopes of the decay curves and correlated with the time to 50% clot lysis.

To determine the effect of the band 3 protein—ligand interaction inhibitors on plasma fibrinogen, 5 $\mu$l of an 80 $\mu$g/ml solution of each inhibitor in 0.001N HCl, 0.011% Tween 80, 50 mM Tris (pH 8.0), and 250 mM NaCl plus 25 $\mu$l of phosphate-buffered saline is incubated with 50 $\mu$l of assayed reference plasma (Helena Laboratories) for various times. The level of plasminogen in the plasma is determined by the change in clotting time upon addition of 10 $\mu$l of 3 units/ml of bovine thrombin (Miles Laboratories) essentially by the method of Clauss, 1957, Acta Haematol. 17:237. The data is reported as the amount of fibrinogen degraded in the plasma sample.

In the fibrin lysis assay, the effect of the band 3 protein—ligand interaction inhibitors on plasmin activity is detected by the appearance of a zone of clearance developing (due to fibrin dissolution) in a fibrin-agarose gel. The gel is made in a 1% low gelling temperature agarose gel, buffered in 0.1M Tris HCl pH7.4, 0.15M NaCl, 2 mM $CaCl_2$ by adding plasminogen-free fibrinogen dissolved in 0.9%(w/v) NaCl, to a final concentration of 1 mg/ml. Six units of thrombin are added to convert the fibrinogen to fibrin and the solution is then poured onto a sheet of GEL-BOND™ and left to set. Before use, wells are punched in the gel and the agarose plugs are removed. Samples of 5–10 $\mu$l are loaded into the wells and the gel is incubated in a humidity chamber at 37° C. overnight (17–20 hours), or for an appropriate time for a zone of lysis to appear. The gel is then soaked in 7.5% acetic acid for 1 hour, stained in fast green (2% solution) for 1–10 minutes and then destained with 40% methanol, 10% acetic acid for at least 2 hours. The gel is then drained and placed at 37° C. overnight to dry. The diameter of the zones of lysis can be measured and compared to those made by standards e.g. plasminogen activated with tPA or u-PA.

IX. Pharmaceutical Compositions and Administration

Inhibitors of the band 3 protein—ligand interaction are useful for enhancing thrombolysis in a mammalian patient, including humans. For such in vivo use, the peptides and inhibitors of the invention are administered in pharmaceutical compositions. The dose administered to a patient should be sufficient to effect a beneficial therapeutic response in the patient, either in the short term or over time. The dose will be determined by the efficacy of the particular interaction inhibitor employed and the condition of the patient, as well as the body weight of the patient to be treated. The size of the dose also will be determined by the existence, nature, and extent of any adverse side-effects that accompany the administration of a particular inhibitor in a particular patient. In determining the effective amount of the inhibitor to be administered, the physician evaluates circulating plasma levels of the inhibitor, toxicities, progression of the disease, and the production of anti-inhibitor antibodies. Inhibitors of the present invention can be administered at a rate determined by the LD-50 of the inhibitor and the side-effects of the inhibitor at various concentrations, as applied to the mass and overall health of the patient. Administration can be accomplished via single or divided doses.

For purposes of treating a mammalian patient, preferably a human, suffering from a condition involving thrombosis, embolism, or other disorders which could benefit from thrombolytic therapy, the inhibitors of the invention are administered on a regular (e.g., daily) basis at a concentration effective to enhance thrombolysis. While an appropriate amount for use with any given patient will depend upon a number of factors and may be readily be determined empirically, in general in an amount of at least about 0.1 mg/kg to about 20 mg/kg of patient body weight, preferably about 1 to about 10 mg/kg, and most preferably about 1 mg/kg to about 5 mg/kg of patient body weight, administered intravenously in physiologic saline or orally is generally effective. Since D-isomers are a non-naturally occurring peptide form, it is anticipated that the D-isomer forms of peptides used as thrombolytics will be metabolized more slowly, and thus persist longer in the circulation. It is therefore anticipated that the D-isomers will be effective in smaller or less frequent doses than those which will be required for the corresponding L-isomers. D-isomers will therefore likely be preferred in some clinical applications.

Pharmaceutically acceptable carriers for band 3 protein—ligand interaction inhibitors are determined in part by the particular composition being administered, as well as by the particular method used to administer the composition. Accordingly, there is a wide variety of suitable formulations of pharmaceutical compositions of the present invention.

Inhibitors of the band 3 protein—ligand interaction, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like. Oral formulations can be made, which include suitable components in a liquid or tablet form. In a preferred embodiment, the oral formulations chosen will permit quick dissolution of the tablet to permit rapid absorption and availability. Formulations for such purposes are well known in the art.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, intraperitoneally, intravesically, intrathecally, or transdermally. Injection solutions and suspensions can be prepared from sterile powders, granules, and tablets of the kind previously described.

The therapeutic benefits of intravenous infusion of synthetic peptides (usually at doses of ~500 $\mu$g in rodents) have been demonstrated in a number of contexts, such as the following: in a mouse model wherein metastasis of liver and lung tumors was reduced (Saiki et al., *Japanese J. Cancer Research* 84:326–335 (1993); Saiki et al., *Japanese J. Cancer Research* 84:558–565 (1993); Komuzawa et al., *Biological & Pharmaceutical Bull.* 16:997–1003 (1993)); in reducing the recruitment of leukocytes into the subarachnoid space in a meningitis model (Sandros et al., *Microbial Pathogenesis* 16:213–220 (1994)); in blocking neovascularization in the rat cornea (Tolsma et al., *J. Cell Biol.* 122:497–511 (1993); and in inhibiting platelet adhesion in vivo (Ito et al., *Int. J. Artificial Organs* 15:737–45 (1992)). It is therefore anticipated that thrombolytic therapy with synthetic peptides at very low doses (i.e., milligrams to obtain micromolar plasma levels) will be effective in vivo in enhancing thrombolysis.

EXAMPLES

The following examples are provided by way of illustration only and not by way of limitation. Those of skill in the art will readily recognize a variety of noncritical parameters that could be changed or modified to yield essentially similar results.

Example 1

The scrambled sequence of peptide 3d was used as a control, LYPQHKT (peptide 3ds) (SEQ ID NO:16). Peptides were synthesized by Coast Scientific (San Diego, Calif.) using the tboc method followed by HF release. All peptides were >97% pure as determined by HPLC and mass spectrometry. PEPSCANs of putative exofacial regions were performed with decapeptides constructed with an offset of 2 amino acids. Non-cleavable peptides with acetylated C-termini were synthesized on pins by Chiron Mimotope (Australia).

Example 2

This example shows an assay for determining the ability of a potential band 3—ligand inhibitor to interfere with adhesiveness of red blood cells. The adherence of sickle and normal red cells to cultured human umbilical vein endothelial cells (HUVEC) was examined using a modified assay based upon a procedure reported in the literature [Hebbel et al. *Blood* 65:2634 (1992)]. A 2.5% suspension of red cells in Hank's Buffered Saline containing 0.5% Bovine Serum Albumin was incubated with or without peptide for 40 minutes at 37° C. in 15 mm diameter plastic wells coated with a confluent monolayer of endothelial cells. The medium was removed and the wells gently washed 3 times with the incubation buffer. Adherent red cells were then visually counted at 100× in an inverted phase microscope using a 25 mm$^2$ grid centrally placed beneath the wells. The binding of sickle cells was 2 to 3 fold higher than that of control red cells: 2.4±0.5 (n=49 separate experiments; 9 patients). No significant difference in this binding result was observed when autologous plasma was substituted for the incubation buffer.

Since the presence of plasma rendered the visualization of the bound red cells difficult, the following experiments were carried out in the absence of plasma. The peptide designated 2f, FSFCETNGLE [SEQ ID NO:26] (residues 476–485 from band 3 extracellular loop 2) and the peptide designated 3d, GHPLQKTY [SEQ ID NO:12] (residues 547–553 from band 3 extracellular loop 3), both in the L-isomeric form and at 25 µg/ml, inhibited abnormal sickle cell binding by 95±13% (n=10; 5 patients) and 102±12% (n=17; 7 patients), respectively. This inhibitory activity was also observed in the presence of plasma. The D-isomer of peptide 3d, 3d(D), was as effective as its L-isomer in inhibiting sickle cell binding: 100±11% (n=15; 5 patients). For the above three active peptides, inhibition was maximal at 20 µg/ml, and 50% inhibition occurred at 4 µg/ml—the same concentration required for half-maximal inhibition of the binding of *P. falciparum*-infected red cells. A control scrambled sequence of peptide 3d, 3ds (LYPQHKT) [SEQ ID NO:16] at 42 µg/ml was only weakly inhibitory, 15±21% (n=15; 7 patients) and a control sequence from another connecting loop of band 3 membrane domain, 7e (KPPKYHP) [SEQ ID NO:14] (residues 814–820), was ineffective at 42 µg/m]: 12±21% (n=11; 4 patients). The peptides 2f and 3d (and not the control peptides 3ds and 7e) were also effective in blocking the cytoadherence of normal cells previously loaded with 10 µM calcium, which has been reported to mimic sickle cell adhesiveness [Hebbel et al. supra (1980)].

Because the peptide 3d binds to endothelial cells, the inhibition of cytoadherence is presumed to arise from competitive binding. These observations imply that in sickle cells at least two segments of the membrane domain of band 3 contribute to the sickle cell's abnormal adherence. They also suggest that in sickle cells band 3 has undergone a conformational rearrangement that exposes normally inaccessible connecting loops between transmembrane helices. In direct support of this conclusion, FACS scan analysis of 3 sickle patients revealed that the monoclonal antibodies IC4 and 4A3 (directed against a normally cryptic band 3 loop sequence exposed in *P. falciparum*-infected red cells) recognized a significant fraction of red cells from human patients suffering from sickle cell disease.

Example 3

This example shows a direct visualization assay for testing the antiadhesiveness effect of a putative inhibitor of the band 3—ligand interaction using human sickle cells (SS). Freshly obtained human SS RBC were washed with PBS, separated from white cells and platelets using Ficoll sedimentation, and brightly fluorescently labeled with 2',7',-bis-(2-carboxyethyl)-5(and 6-)carboxyfluorocescein (BCECF) (Molecular Probes, Inc., Eugene, Oreg.) in vitro. BCECF stock solution that contained 0.5 mg of the fluorophor in 1 ml. Dimethyl sulfoxide (DMSO) was prepared on the day of the experiment and 30 µl of this solution was added to 1 ml. of a 5% hematocrit suspension of red cells. This suspension was incubated at 37° C. for 1 hour. After incubation, the cells were washed with 10 ml of PBS, centrifuged, and resuspended to 1 ml. in PBS for i.v. administration in 0.1 aliquots.

Male C57B6 mice were anaesthetized and the microcirculation of the cremaster muscle was exposed as previously described (Maly et al., Cell 86:643–653 (1996); see also von Andrian, U., Microcirculation 3:287–300 (1996)) on the stage of an intravital microscope (IV-500, Mikron Instruments, San Diego, Calif.) equipped with a video-triggered stroboscopic epifluorescent light source. The tissue was physiologically maintained by superfusion with warmed endotoxin-free, isotonic buffer. Femoral and carotid artery catheters provided access for infusion of labeled RBC and biologic reagents. Adhesive events were directly visualized as labeled cells pausing in contact with the epithelium of post-capillary venules for >1 second. Single vessels were observed and an adhesive index (AI) calculated as the adhesive events/labeled cells×10$^{-3}$ entering the vessel. Initial studies with untreated animals showed a small but distinct increase in AI with SS cells (AI 2.3±0.9, n=17).

Further studies were conducted employing infusions of 75 μg of band 3 -ligand interaction inhibitors in 0.1 cc phosphate buffered saline (PBS). These studies showed that both peptides 2f and 3d inhibited SS adhesiveness. Moreover, they showed that the D-isomer form of the 3d peptide, 3dD, also inhibited SS adhesiveness. On the other hand, a variant peptide of 3d using the same amino acids but in a scrambled order, showed no effect on SS adhesiveness. The adhesiveness of the cells could be increased by administration of 2 ng of platelet activating factor, making any reduction in adhesiveness due to the interaction inhibitors easier to detect.

Example 4

This example shows the activity of interaction inhibitors in enhancing thrombolysis in vivo. Mice were anaesthetized and prepared as for the adhesiveness experiments set forth above. In separate experiments, the animals were infused with 75 μg in 0.1 cc PBS of interaction inhibitors 3d, 3dD (the all D-isomer version of 3d), and 3dS (a version of 3d containing the same amino acids but in a scrambled order). All animals treated with 3d or 3dD developed bleeding at suture sites within 10 minutes of infusion. The bleeding continued for approximately one-half hour, and then ceased. Bleeding could be reinduced with a second infusion of the inhibitors.

Example 5

This example shows the use of an interaction inhibitor in a human patient. A 70 kg human patient with acute venous or arterial thrombosis or embolism is administered 210 mg (3 mg/kg) of peptide 3d (GHPLQKTY [SEQ ID NO:12]), in a sterile saline solution, i.v. The patient is observed for undesired bleeding. If the thrombotic or embolic condition is not resolved, the patient is reinfused with one or more additional doses of inhibitor according to the clinical judgment of the physician or other health care practitioner.

Example 6

A 70 kg human patient with known arterial sclerotic cardiovascular disease or unstable angina is provided with tablets containing 210 mg of peptide 3d (GHPLQKTY [SEQ ID NO:12]) in a quickly dissolving formulation. The patient develops crushing substernal chest pain and calls his physician. After determining the patient's clinical status, the physician instructs the patient to take one 210 mg. tablet of peptide 3d and then to have himself transported to the nearest medical center.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A method of enhancing thrombolysis in a mammal comprising administering to the mammal an amount of an inhibitor of protein band III—ligand interaction sufficient to enhance thrombolysis.

2. The method of claim 1 wherein the inhibitor of band 3 protein—ligand interactions comprises a substantially pure loop 2 peptide or a conservatively substituted variant thereof, or a reverse sequence of such a peptide.

3. The method of claim 1 wherein the inhibitor of band 3 protein—ligand interactions comprises a peptide characterized by the sequence motif $Z^2Z^3Z^2$ UX⁻UUU$\underline{U}$X⁻ (SEQ ID NO:44), wherein $Z^2$ represents a hydrophobic residue, U represents unobstructive residues, $Z^3$ is either $Z^2$ or an unobstructive residue and X⁻ represents negatively charged residues, or a reverse sequence of this sequence motif.

4. The method of claim 3 wherein the peptide is about 50 or fewer amino acids.

5. The method of claim 3 wherein the peptide is about 12 or fewer amino acids.

6. The method of claim 3, wherein the hydrophobic residue is phenylalanine.

7. The method of claim 3 wherein X⁻ is independently selected from the group consisting of glutamic acid and aspartic acid.

8. The method of claim 3, comprising a sequence selected from the group consisting of FSFCETNGLE (SEQ ID NO:26), ASFCETNGLE (SEQ ID NO:29), FAFCETNGLE (SEQ ID NO:30), FSACETNGLE (SEQ ID NO:31), FSFA-ETNGLE (SEQ ID NO:32), FSFCEANGLE (SEQ ID NO:34), FSFCETAGLE (SEQ ID NO:35), FSFCETNALE (SEQ ID NO:36), and FSFCETNGAE (SEQ ID NO:37), or a reverse sequence of these sequences.

9. The method of claim 3, wherein the peptide is substantially identical to the amino acid sequence FSFCETNGLE (SEQ ID NO:26), or a reverse sequence of that sequence.

10. The method of claim 3, wherein the sequence motif has the sequence FSFCETNGLE (SEQ ID NO:26).

11. The method of claim 3, wherein the peptide comprises all D-amino acids.

12. A method according to claim 3 wherein the peptide is administered in an amount of about 0.1 mg/kg to about 20 mg/kg of patient body weight.

13. A method according to claim 3 wherein the peptide is administered in an amount of about 1 mg/kg to about 5 mg/kg of patient body weight.

14. The method of claim 1 wherein the inhibitor of band 3 protein—ligand interactions is a substantially pure loop 3 peptide or a conservatively substituted variant thereof, or a reverse sequence of a loop 3 peptide.

15. The method of claim 1, wherein the inhibitor of band 3 protein—ligand interactions comprises a peptide characterized by the sequence motif $Z^1$UKUUUX⁺ (SEQ ID NO:45), wherein $Z^1$ is selected from the group consisting of tyrosine, phenylalanine and alanine; K is a lysine residue; U represents unobstructive residues; and X⁺ is a positively charged residue, or a reverse sequence of such a sequence motif.

16. The method of claim 15 wherein the peptide is about 50 or fewer amino acids.

17. The method of claim 15 wherein the peptide is about 12 or fewer amino acids.

18. A method according to claim 15, wherein $Z^1$ is selected from the group consisting of tyrosine and phenylalanine.

19. A method according to claim 15, wherein X⁺ is selected from the group consisting of lysine and histidine.

20. A method according to claim 15, wherein the peptide is selected from the group consisting of FVKRVKTY (SEQ ID NO:15), and HALQKTY (SEQ ID NO:19), or a reverse sequence of these sequences.

21. The method of claim 15, wherein the peptide comprises all D-amino acids.

22. A method according to claim 15, wherein the peptide is administered in an amount of about 0.1 mg/kg to about 20 mg/kg of patient body weight.

23. A method according to claim 15, wherein the peptide is administered in an amount of about 1 mg/kg to about 5 mg/kg of patient body weight.

24. The method of claim 1, wherein the inhibitor of band 3 protein—ligand interaction comprises a peptide YVKRVK (SEQ ID NO:2), or a reverse sequence of this sequence.

25. The method of claim 24, wherein the peptide consists of all D-amino acids.

26. A method according to claim 24, wherein the peptide is administered in an amount of about 0.1 mg/kg to about 20 mg/kg of patient body weight.

27. A method according to claim 24, wherein the peptide is administered in an amount of about 1 mg/kg to about 5 mg/kg of patient body weight.

28. The method of claim 1, wherein the inhibitor of band 3 protein—ligand interaction comprises a peptide selected from the group consisting of DHPLQKTYNY (SEQ ID NO:6), KLIKIFQKHPLQKTY (SEQ ID NO:8), DVPYVKRVKTWRMH (SEQ ID NO:10), GHPLQKTY (SEQ ID NO:12), YTKQLPHG (SEQ ID NO:13), FQDH-PLQKTYNY (SEQ ID NO:17), HPAQKTY (SEQ ID NO:20), HPLAKTY (SEQ ID NO:21), HPLQKAY (SEQ ID NO:23) and HPLGQKTY (SEQ ID NO:25), or a reverse sequence of these sequences.

29. The method of claim 28, wherein the peptide consists of all D-amino acids.

30. A method according to claim 28, wherein the peptide is administered in an amount of about 0.1 mg/kg to about 20 mg/kg of patient body weight.

31. A method according to claim 28, wherein the peptide is administered in an amount of about 1 mg/kg to about 5 mg/kg of patient body weight.

* * * * *